(12) United States Patent  (10) Patent No.: US 8,320,728 B2
Mizaikoff et al.  (45) Date of Patent: Nov. 27, 2012

(54) FILM THIN WAVEGUIDES, METHODS OF FABRICATION THEREOF, AND DETECTION SYSTEMS

(75) Inventors: Boris Mizaikoff, Atlanta, GA (US); Christy Charlton, Atlanta, GA (US); Jerome Faist, Neuchatel (CH); Marcella Giovannini, Neuchatel (CH)

(73) Assignee: Georgia Tech Research Corporation, Atlanta, GA (US)

( * ) Notice: Subject to any disclaimer, the term of this patent is extended or adjusted under 35 U.S.C. 154(b) by 826 days.

(21) Appl. No.: 12/065,948

(22) PCT Filed: Sep. 8, 2006

(86) PCT No.: PCT/US2006/035104
§ 371 (c)(1),
(2), (4) Date: Dec. 22, 2008

(87) PCT Pub. No.: WO2007/030737
PCT Pub. Date: Mar. 15, 2007

(65) Prior Publication Data
US 2009/0206242 A1    Aug. 20, 2009

Related U.S. Application Data

(60) Provisional application No. 60/715,116, filed on Sep. 8, 2005.

(51) Int. Cl.
*G02B 6/10* (2006.01)
*G02B 6/26* (2006.01)
*G01J 1/04* (2006.01)

(52) U.S. Cl. ........ 385/131; 385/129; 385/130; 385/132; 385/30; 250/227.11

(58) Field of Classification Search .......... 385/129–132, 385/30; 250/227.11
See application file for complete search history.

(56) References Cited

U.S. PATENT DOCUMENTS

| | | | |
|---|---|---|---|
| 4,776,655 A * | 10/1988 | Robertson et al. | 385/130 |
| 5,797,445 A * | 8/1998 | Westbrooks et al. | 165/11.1 |
| 6,654,533 B1 * | 11/2003 | Koteles et al. | 385/131 |

* cited by examiner

*Primary Examiner* — Brian M. Healy
*Assistant Examiner* — Guy Anderson
(74) *Attorney, Agent, or Firm* — Thomas Horstemeyer, LLP (57) ABSTRACT

Briefly described, embodiments of this disclosure, among others, include solid state, thin film waveguides, detection systems including waveguides, and methods of detecting target compounds.

12 Claims, 5 Drawing Sheets

FILM THIN WAVEGUIDES, METHODS OF FABRICATION THEREOF, AND DETECTION SYSTEMS

CROSS-REFERENCE TO RELATED APPLICATION

This application is related to U.S. Provisional Application entitled "Planar mid-infrared single mode waveguides" Ser. No. 60/715,116, filed on Sep. 8, 2005, which is entirely incorporated herein by reference.

STATEMENT REGARDING FEDERALLY SPONSORED RESEARCH OR DEVELOPMENT

This invention was made with government support under National Institutes of Health Contract #1 R01 EB000508-01A1 (GT # G-33-B26) and National Science Foundation Contract # OISE-0420005 (GT# G-33-B97). The government has certain rights in the invention.

FIELD OF THE DISCLOSURE

The present disclosure relates generally to waveguides and detection systems.

BACKGROUND

The mid-infrared (MIR, about 2 to 20 µm) spectral band is particularly useful for molecular sensing applications due to the excitation of fundamental rotational and vibrational transitions allowing for sensitive and selective detection of molecules in both gas and liquid phases. For liquid sensing, attenuated total reflection (ATR) and evanescent field absorption measurements facilitate probing of samples, which are too opaque for transmission absorption measurements such as in environmental monitoring, process analysis, and biological applications.

If total internal reflection (TIR) occurs, an evanescent field extends at the interface between the optically denser waveguide (refractive index $n_1$) and an optically thinner adjacent medium (refractive index $n_2$; with $n_1 > n_2$). The penetration depth, $d_p$, of the evanescent field is commonly defined as:

$$d_p = \lambda/2\pi(n_1^2 \sin^2\theta - n_2^2)^{1/2},$$

where $\lambda$ is the wavelength of the radiation, and $\theta$ is the incoupling angle. Absorbing species present within the penetration depth of the evanescent field interact with radiation, resulting in attenuation of the frequencies where resonant energy transfer to the vibrational modes of molecules occurs.

As the intensity of the evanescent field strongly depends on the waveguide geometry, decreasing the fiber diameter or tapering a section of the fiber increases the intensity of the evanescent field, and thereby improves the sensitivity to absorbing species at or close to the waveguide surface. Evanescent field absorption measurements follow a pseudo Lambert-Beer relationship, where the absorbance A is defined as:

$$A = (\epsilon Cl)r$$

where $\epsilon$ is the molar absorptivity, C is the concentration, l is the optical path length, and r is the fraction of power guided outside the waveguide core. Maximum evanescent field intensity, and therefore a maximum value of r, would occur in a single mode waveguide, which is thickness-matched to the emission frequency of a corresponding laser light source. Ideal optimization conditions are limited to mono-mode laser light sources providing a platform for highly integrated MIR evanescent field sensing systems.

Laser light sources provide enhanced spectral density compared to conventional broadband MIR sources. Consequently, if a narrow emission band is matched to a carefully selected absorption band characteristic for the analyte of interest, sufficient selectivity but higher sensitivity can be achieved in a more compact and miniaturizable sensing system.

Quantum cascade lasers (QCLs) have successfully been applied in sensing formats due to their wide coverage of MIR emission frequencies. Distributed feedback (DFB) QCLs provide narrow emission line-width (approximately 0.006 $cm^{-1}$) by incorporating a grating exposed or buried at the surface of the laser ridge, thus facilitating selection of overlapping analyte bands.

SUMMARY

Briefly described, embodiments of this disclosure, among others, include solid state, thin film waveguides, detection systems including waveguides, methods of detecting target compounds, and the like.

One exemplary solid state, thin film waveguide, among others, includes: a substrate having a core layer disposed thereon, the core layer has a thickness of about 2 to 1000 µm, wherein the core layer is made of a material selected from: group III-V materials, composites thereof, and combinations thereof.

Another exemplary solid state, thin film waveguide, among others, includes: a substrate, a cladding layer, and a core layer, wherein the cladding layer is disposed on the substrate, wherein the core layer is disposed on the cladding layer, wherein the combination of the thickness of the core layer and the cladding layer is about 2 to 1000 µm, wherein the core layer is made of a first material selected from: group III-V materials, composites thereof, and combinations thereof, wherein the cladding layer is made of a second material selected from: group III-V materials, composites thereof, and combinations thereof, wherein the core layer and the cladding layer have different refractive indices.

One exemplary detection system, among others, includes: a light source system; a solid state, thin film waveguide interfaced with the light source, wherein the solid state, thin film waveguide includes a core layer, wherein the core layer is made of a first material selected from: group III-V materials, composites thereof, and combinations thereof, wherein the core layer has a thickness of about 2-20 µm; and a detector system interfaced with the solid state, thin film waveguide.

One exemplary method of detecting a target compound, among others, includes: providing a detection system as described herein; directing light from the light source system through the solid state, thin film waveguide; and detecting the target compounds using the evanescent field of the light protruding from the solid state, thin film waveguide.

Other systems, methods, features, and advantages of this disclosure will be or become apparent to one with skill in the art upon examination of the following drawings and detailed description. It is intended that all such additional systems, methods, features, and advantages be included within this description, be within the scope of this disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 3A and 3B illustrate top views of two detector systems.

DETAILED DESCRIPTION

Embodiments of the present disclosure will employ, unless otherwise indicated, techniques of physics, chemistry, biochemistry, biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, surface coatings, recognition chemistries with chemical, biochemical, biological, and/or synthetic/biomimetic receptors, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Discussion

Embodiments of the present disclosure include solid state, thin film waveguides, methods of making waveguides, detection systems including waveguides, methods of detecting target compounds, and the like. Embodiments of the present disclosure use evanescent field absorption to directly detect target compounds (e.g., disposed on the surface of the waveguide), indirectly through the target compounds interaction with surface modifications (e.g., surface recognition chemistries, biologies, and the like) at the surface of the solid state, thin film waveguide, and/or indirectly through the target compounds interaction with recognition elements not immobilized at the surface of the waveguide (e.g., recognition chemistries, biologies, and the like) but within the penetration depth of the evanescent field protruding from the surface of the solid state, thin film waveguide. Therefore, label free detection of target compounds can be performed using embodiments of the present disclosure. In particular, embodiments of the present disclosure enable label free detection of target compounds in the mid-infrared region of the spectrum.

In addition, to take advantage of maximizing the radiation energy in the evanescent field for maximum sensitivity at the waveguide surface, the waveguide thickness should approach the order of magnitude of the supported wavelength. In other words, if a single-mode light source such as a laser (e.g., a quantum cascade laser) is used, the waveguide should ideally support a light single-mode, thereby maximizing the amount of energy available in the evanescent tail of the mode guided at the interface to the adjacent medium, if the right refractive index contrast is provided.

Embodiments of the solid state, thin film waveguides can be tailored to a thickness to support guiding a single light mode emitted from a light source positioned adjacent the solid state, thin film waveguide. Optimizing the solid state, thin film waveguide to support single mode propagation can be advantageous because it maximizes the energy guided in the evanescent field, and thus enhances the detection limits (e.g., detection of a monolayers on the surface of the waveguide or the interaction of a small number of molecules with recognition elements immobilized on and/or within the penetration depth of the evanescent field protruding from (e.g., chemical and/or biological recognition elements, and the like) the surface of the waveguide) of embodiments of the present disclosure. Furthermore, tailoring of the refractive index contrast by varying the material composition of the single-mode waveguide enables deliberately designing the penetration depth of the mode and whether it is guided closer to the surface or penetrates deeper into the adjacent medium. Such superior control on the evanescent field is maximized with a single-mode waveguide.

In another embodiment, the solid state, thin film waveguide can support multiple wavelengths. For example, a single solid state, thin film waveguide can support different wavelengths of light emitted from one or more light sources. Due to the lateral confinement of the radiation propagating along the planar waveguide structure that is achieved with the described embodiments, several different wavelengths provided by one or more light sources can be propagated without mixing in parallel through the same waveguide structure (e.g., physical separation and optical insulation of individual waveguides may not be necessary) thus facilitating a multiplexed sensing platform, which is based on an inherently integrated wavelength chip supporting the propagation of laterally confined different wavelengths in parallel. For each wavelength, the surface of the waveguide may be locally modified with individual molecular recognition chemistries along the propagation path. Thereby, the entire multiplexed sensing chip may be supported with e.g., a single (micro) fluidic sample transport solution, as the local confinement of the radiation propagation path ensures distributed readout of the evanescent field absorption at individual wavelengths.

Alternatively, several frequencies may be coupled into the same radiation propagation path, without lateral separation (e.g., by coupling radiation form a multi-wavelength or broadband light source into the described waveguide embodiment). In order to de-convolute the spectral response into a wavelength dispersed spectrum, a dispersive element (e.g., grating, prism, and the like) or modulated/demodulated radiation (e.g., by an interferometer, etc.) utilizing e.g., Fourier transform techniques.

Embodiments of the present disclosure enable chemical sensing of target compounds in at least the mid IR spectral range (e.g., about 2 to 20 µm) and can include chemical sensing up to the far IR spectral range (e.g., about 2 to 1000 µm and any range within this wavelength range, which can include, but is not limited to, about 2 to 5, about 2 to 12, about 5 to 8, about 5 to 12, about 5 to 15, about 5 to 20, about 8 to 12, about 8 to 15, about 8 to 20, about 2 to 15, about 2 to 20, about 10 to 20, about 10 to 50, about 20 to 50, about 20 to 100, about 50 to 100, about 50 to 200, and about 100 to 1000 µm). The thickness of the solid state, thin film waveguide can be appropriately designed to accommodate the one or more wavelengths in the spectral range of interest.

Chemical sensing in the mid-IR range is advantageous due to the inherent molecular selectivity resulting from the excitation of fundamental rotational and vibrational modes. In addition, embodiments of the present disclosure enable chemical sensing in the about 8 to 20 µm spectral range, which provides access to the unique absorption patterns characteristic for many organic compounds. Furthermore, embodiments of the present disclosure with an appropriate material composition enable chemical sensing in the about 20 to 1000 µm spectral range, which provides access to vibrational patterns of larger molecules, biomolecules, polymers, biopolymers, peptides, crystals, and the like.

In a non-limiting embodiment, the light source is a quantum cascade laser that can be selected to emit at a single mode (e.g., a specific mode in mid-infrared (IR) spectral range). The wavelength of the laser can be selected anywhere in the mid-IR range (e.g., about 2 to 12, about 5 to 8, about 5 to 12, about 5 to 15, about 5 to 20, about 8 to 12, about 8 to 15, about 8 to 20, about 2 to 15, about 2 to 20, and about 10 to 20), which enables tailoring of the wavelength with the thickness of the solid state, thin film waveguide (e.g., the thickness is about equal to the wavelength). Combining the quantum cascade laser with the solid state, thin film waveguide takes advantage of the single mode emission of the quantum cascade laser and maximizes the energy guided in the evanescent field. In addition, the quantum cascade laser/solid state, thin film waveguide combination is advantageous in the mid-IR spectrum because the wavelength of interest can be probed by selecting the appropriate quantum cascade laser having the wavelength of interest and tailoring the thickness of the solid state, thin film waveguide to the mode of interest (e.g., the thickness is about equal to the wavelength of interest). Additional details are described in Example 1.

The solid state, thin film waveguide can be a symmetric waveguide or an asymmetric waveguide. The symmetric waveguide includes a core layer disposed on a substrate, without a cladding layer. The light wave is symmetrically positioned within the core layer so that equal portions of the evanescent tail or field of the light wave (e.g., the portion used in evanescent field absorption) extend out of the top and bottom of the core layer. The distance that the evanescent field extends from the core layer depends upon the wavelength, the thickness of the core layer, the material of the core layer, and the refractive index contrast between the core layer and the adjacent medium. The symmetric waveguide can be tailored by adjusting one or more of these characteristics.

The asymmetric waveguide includes the core layer disposed on a cladding layer, which is disposed on the substrate. The light wave is asymmetrically positioned within the core layer and the cladding layer so that unequal portions of the evanescent tail of the light wave extend out of the top and bottom of the core layer (e.g., See FIG. 4). The asymmetric position of the light wave enables a greater portion of the light wave tail to extend from the core layer, while little or no portion of the light wave tail extends into the substrate. Reducing or eliminating a portion of the light wave tail extending into the substrate reduces light energy loss. The distance that the evanescent field extends from the core layer depends upon the thickness of each of the core layer and the cladding layer, the material of each of the core layer and the cladding layer, and the refractive index ratio of the core layer and the cladding layer.

In general, a substance of interest (e.g., liquids, solids, gases, supercritical fluids, and the like) is disposed on or comes into close proximity with (e.g., interacts with a surface modification or a recognition element within the penetration depth of the evanescent field) a portion of the solid state, thin film waveguide. For example, the substance of interest is a liquid that includes target compounds to be detected. However, it may also be a gas, a solid, another aggregation state, and/or mixtures thereof (e.g., aerosols, emulsions, suspensions, and the like). Then, a light source directs light into the solid state, thin film waveguide. The evanescent field interacts with the target compounds in the liquid disposed on the surface of the solid state, thin film waveguide (e.g., with or without immobilized chemistry at the waveguide surface (e.g., a complementary DNA strand, a receptor, a complexing agent, and the like) and/or with or without recognition chemistry (e.g., a complementary DNA strand, a receptor, a complexing agent, and the like) in the solution, both can create a—more or less specific—measurable change to be detected in the 2-1000 µm range or other ranges as described herein). The target compounds can be bound or immobilized on the surface and/or unbound but within the penetration depth of the evanescent field. A detector disposed at the end of the solid state, thin film waveguide detects the interaction of the light with the target compounds. An optic system can be disposed between the light source and the solid state, thin film waveguide and/or between the solid state, thin film waveguide and the detector. Appropriate optic systems can be selected for the particular application and set up. Alternatively, the entire detection system may be fully integrated (e.g., hybridized or monolithically, and any variation thereof) including light source(s), waveguide(s), and detector(s), with/without optic systems, and with/without sample compartment and/or sample transportation embodiments. The detected interaction can be correlated to the identity and/or quantity of the target compound.

Embodiments of the present disclosure can be used to detect target compounds, such as, but not limited to, compounds that have a vibrational or rotational pattern. In particular, the target compound can include, but is not limited to, chemicals, biomolecules, entire biological organisms, whole cells, membranes, tissues, and the like. In particular, the target compounds can include, but are not limited to, halogenated hydrocarbons, aromatic hydrocarbons, volatile organic compounds, surfactants, polycyclic aromatic hydrocarbons (PAHs), pesticides, macromolecules, pathogens, toxins, nerve agents, chemical/biochemical/biological warfare agents, antigens, proteins, enzymes, DNA, RNA, viruses, spores, bacteria, cells, neurotransmitters, signaling molecules, metabolites, and the like.

Figure 1A:
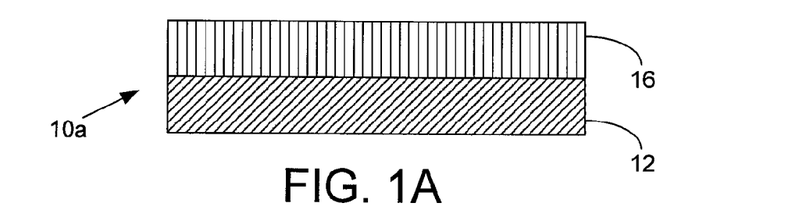
FIG. 1A through FIG. 1C illustrate embodiments of illustrative embodiments of solid state, thin film waveguides.
Figure 1B:
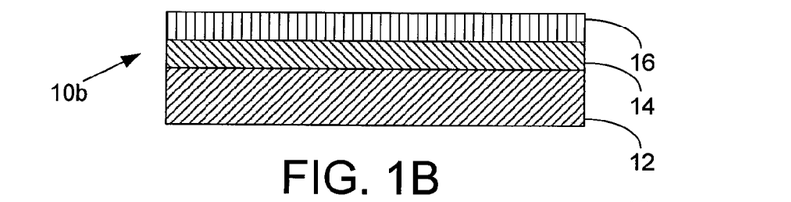
Figure 1C:
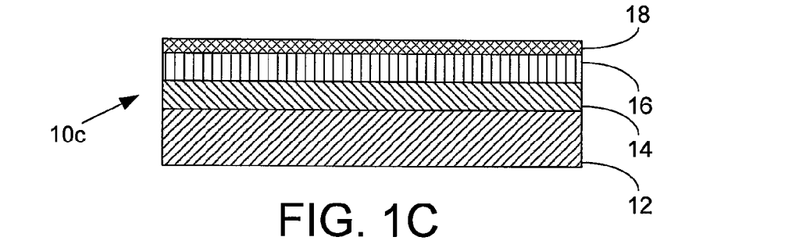

FIG. 1A through FIG. 1C illustrate embodiments of the solid state, thin film waveguides 10a through 10b (hereinafter "thin film waveguides" 10a through 10b). FIG. 1A illustrates an embodiment of a symmetrical thin film waveguide 10a that includes, but is not limited to, a substrate 12 and a core layer 16. The core layer 16 is disposed on a portion of the substrate 12. The substrate can be made of materials such as, but not limited to, silicon, silicon compounds, germanium, germanium compounds, gallium, gallium compounds, indium, indium compounds, or other semiconductor materials/compounds, and substrates such as sapphire, SiC, and the like. The substrate 12 can have a thickness of about 1 μm to 10 cm. The length and width of the substrate 12 can vary depending on the particular application, but is typically at least as long as the thin film waveguide.

The core layer 16 can be made of materials transparent or substantially transparent to specified wavelengths of light and have a refractive index appropriate for the specified wavelengths. Another factor that may be considered upon selection of the core layer 16 is the thickness of the core layer, which is described in more detail below.

In general, the core layer 16 can be made of materials or material composites (at various ratios) such as, but not limited to, group III-V materials, composites thereof, and combinations thereof. In particular, the core layer 16 can include materials or material composites such as, but not limited to, GaAs, AlGaAs (e.g., $Al_xGa_{1-x}As$, where x is from 0.001 to 0.999), AlAsSb, InAs, InP, InSb, Sb, InSb, AlAs, AlInAs, GaInAs, AlSb, GaSb, InAs, SiGe, GaN, AlN, AlGaN, InGaN, and GaP. It should be noted that the ratio of the components in the materials or composites thereof can be at any chemically appropriate ratio as known in the art. For example, $Ga_xAs_{x-1}$, $Al_xGa_{1-x}As$, $Al_xAs_{x-1}Sb$, and so on, where x is from 0.001 to 0.999. It should be noted that subscripts are not included for each of the compounds or composites. This does not indicate that they are present in a 1 to 1 ratio, but rather at a chemically appropriate ratio as known in the art. The core layer 16 can be fabricated using methods such as, but not limited to, molecular beam epitaxy (MBE), metal-organic chemical vapor deposition (MOCVD), hydride vapor phase epitaxy (HVPE), atomic layer deposition (ALD), and the like.

The core layer 16 has a thickness that allows a portion of the light wave to extend outside of the core layer 16. The portion of the light wave that extends out of the core layer 16 enables evanescent field absorption to be conducted. The selection of the thickness of the core layer 16 is a function of the material that the core layer 16 is made of, the wavelength of the light emitted from the light source, the distance from the core layer 16 the light wave is expected to extend, and the length of the core layer 16.

In general, the core layer 16 can have thickness of about 2 to 1000 μm and any range within this wavelength range, which can include, but is not limited to, about 2 to 5, about 2 to 12, about 5 to 8, about 5 to 12, about 5 to 15, about 5 to 20, about 8 to 12, about 8 to 15, about 8 to 20, about 2 to 15, about 2 to 20, about 10 to 20, about 10 to 50, about 20 to 50, about 20 to 100, about 50 to 100, about 50 to 200, and about 100 to 1000 μm.

The core layer 16 length is a function of the wavelength of the light emitted from the light source, the width of the core layer 16 (e.g., the more energy is lost the larger the distance the light wave extends from the core layer 16), and the like. The core layer 16 is confined in length only by the attenuation losses of the selected material, and has a length of about 100 μm to 1000 μm, about 1000 μm to 1 cm, about 1000 μm to 10 cm, about 1 cm to 10 cm, and about 10 cm to 100 cm.

In an embodiment, the core layer 16 has a width no larger than necessary to contain the wavelength of light passed through the core layer 16 (e.g., FIG. 3A) and is termed "a single strip thin film waveguide." In another embodiment, the core layer 16 can be very wide and two or more light sources can pass light through the core layer 16 (e.g., FIG. 3B) and is termed "a planar thin film waveguide." The width is a function of the number of light sources and the wavelength of the light. The light sources are positioned at least a certain distance apart so that the two light sources do not overlap or substantially overlap to interfere with the particular purpose of the thin film waveguide, and radiation propagates laterally confined along the waveguide.

In general, the core layer 12 for a single strip thin film waveguide has a width of, but is not limited to, about 1 μm to 1 cm, about 1 μm to 1000 μm, and about 1 μm to 100 μm. In general, the distance between the light sources in a planar thin film waveguide is nearly zero and up to about 10 cm, however greater distances can be envisioned and can be tailored for a particular application. These two embodiments will be described in greater detail below.

FIG. 1B illustrates an embodiment of an asymmetrical thin film waveguide 10b that includes, but is not limited to, the substrate 12, a cladding layer 14, and the core layer 16. The cladding layer 14 is disposed on the substrate 12 and the core layer 16 is disposed on the cladding layer 14. The substrate 12 is similar to that as discussed in reference to FIG. 1A.

The core layer 16 and the cladding layer 14 can each be made of materials transparent or substantially transparent to specified wavelengths of light. In addition, the core layer 16 and the cladding layer 14 can each be made of materials so that the combination of the core layer 16 and the cladding layer 14 have a refractive index profile appropriate for the specified wavelengths and the shift in the position of the light wave within the core layer 16 and the cladding layer 14 is appropriate for the specified application. Another factor that may be considered upon selection of the core layer 16 and the cladding layer 14 is the thickness of the core layer 16 and the cladding layer 14, which are described in more detail below. The refractive index of the particular compounds or composites are a function of the compounds and composites and the refractive index profile can be tailored to a particular number based on selection of the compounds and/or composites.

In general, the core layer 16 can be made of materials such as, but not limited to, group III-V materials, composites thereof, and combinations thereof. In particular, the core layer 16 can include materials such as, but not limited to, GaAs, AlGaAs (e.g., $Al_xGa_{1-x}As$), AlAsSb, InAs, InP, InSb, Sb, InSb, AlAs, AlInAs, GaInAs, AlSb, GaSb, InAs, SiGe, GaN, AlN, AlGaN, InGaN, and GaP.

In general, the cladding layer 14 can be made of materials such as, but not limited to, group III-V materials, composites thereof, and combinations thereof. In particular, the cladding layer 14 can include materials such as, but not limited to, GaAs, AlGaAs (e.g., $Al_xGa_{1-x}As$), AlAsSb, InAs, InP, InSb, Sb, InSb, AlAs, AlInAs, GaInAs, AlSb, GaSb, InAs, SiGe, GaN, AlN, AlGaN, InGaN, and GaP. The cladding layer 14 can be fabricated using methods such as, but not limited to, molecular beam epitaxy (MBE), metal-organic chemical vapor deposition (MOCVD), hydride vapor phase epitaxy (HVPE), atomic layer deposition (ALD), and the like.

The core layer 16 and the cladding layer 14 can each have a thickness that allows a portion of the light wave to extend outside of the core layer 16 and the cladding layer 14 and minimizes the amount of energy lost (e.g., an asymmetrical light wave distribution where little or no energy is lost to interaction with the substrate 12 (also see FIG. 4 in Example 1)). The portion of the light wave that extends out of the core layer 16 and the cladding layer 14 enables evanescent field absorption to be conducted. The selection of the thickness of the core layer 16 and the cladding layer 14 are a function of the material that the core layer 16 and the cladding layer 14 are each made of, the wavelength of the light emitted from the light source, the distance from the core layer 16 the light wave is expected to extend, and the length of the core layer 16.

In general, the thickness of the core layer 16 and the cladding layer 14 combined is about 2 to 1000 μm and any range within this wavelength range, which can include, but is not limited to, about 2 to 5, about 2 to 12, about 5 to 8, about 5 to 12, about 5 to 15, about 5 to 20, about 8 to 12, about 8 to 15, about 8 to 20, about 2 to 15, about 2 to 20, about 10 to 20, about 10 to 50, about 20 to 50, about 20 to 100, about 50 to 100, about 50 to 200, and about 100 to 1000 μm.

In general, the core layer 16 can have thickness of about 2 to 1000 μm and any range within this wavelength range, which can include, but is not limited to, about 2 to 5, about 2 to 12, about 5 to 8, about 5 to 12, about 5 to 15, about 5 to 20, about 8 to 12, about 8 to 15, about 8 to 20, about 2 to 15, about 2 to 20, about 10 to 20, about 10 to 50, about 20 to 50, about 20 to 100, about 50 to 100, about 50 to 200, and about 100 to 1000 m.

In general, the cladding layer 16 can have thickness of about 2 to 1000 μm and any range within this wavelength range, which can include, but is not limited to, about 2 to 5, about 2 to 12, about 5 to 8, about 5 to 12, about 5 to 15, about 5 to 20, about 8 to 12, about 8 to 15, about 8 to 20, about 2 to 15, about 2 to 20, about 10 to 20, about 10 to 50, about 20 to 50, about 20 to 100, about 50 to 100, about 50 to 200, and about 100 to 1000 μm.

The core layer 16 and the cladding layer 14 length are a function of the wavelength of the light emitted from the light source, the width of the core layer 16 and the cladding layer 14 (e.g., more energy is lost the larger the distance the light wave extends from the core layer 16), and the like. The length of each of the core layer 16 and the cladding layer 14 is confined only by the attenuation losses of the selected material, and each have a length of about 100 μm to 1000 μm, about 1000 μm to 1 cm, about 1000 μm to 10 cm, about 1 cm to 10 cm, and about 10 cm to 100 cm FIG. 1C illustrates an embodiment of an asymmetrical thin film waveguide 10c that includes, but is not limited to, the substrate 12, the cladding layer 14, the core layer 16, and a protective layer and/or recognition layer 18. The cladding layer 14 is disposed on the substrate 12 and the core layer 16 is disposed on the cladding layer 14. The protective layer and/or recognition layer 18 is disposed on the core layer 16.

The protective layer 18 can function to protect the core layer 16 and is at least partially IR transparent. The protective layer 18 can be made of materials such as, but not limited to, $Si_3N_4$, $SiO_2$, diamond, diamond like carbon, polymers, and combinations thereof. The polymers can include, but are not limited to, polyamides, polyimides, (substituted) xylylenes (e.g., parylene), polyaryletherketones, and combinations thereof.

The thickness of the protective layer 18 should be small enough to allow for the compounds of interest to interact with the evanescent field extending from the core layer 16. The protective layer 18 can have a thickness of about 10 nm to 500 nm, but depends at least in part upon the distance that the evanescent field extends from the core layer 16 and the refractive index of the protective layer.

In another embodiment the protective layer 18 can function as a porous or semi-porous layer that allows some compounds to come closer to the core layer 16 and interact with the evanescent field, while not permitting other types of compounds to come close enough to interact with the evanescent field. For example, the protective layer 18 can be hydrophobic, so that hydrophobic compounds can penetrate the protective layer 18 and interact with the evanescent field.

The thickness of the protective layer 18 in this embodiment can vary and depends upon the semi-porous nature of the material of the protective layer 18. The thickness of the protective layer 18 can be a thickness that allows the types of compounds of interest to penetrate through the protective layer 18 and interact with the evanescent field, while not allowing or substantially reducing the amount of the compounds that are not of interest to penetrate through the protective layer 18 and interact with the evanescent field.

The protective layer 18 can be made of materials such as, but not limited to, polymers, sol-gels, ceramics, self-assembled monolayers, biological materials, antibodies, receptors, membranes, and combinations thereof. The polymer can include, but is not limited to, a hydrophobic polymer (e.g., Teflon AF (1601, 2400), poly(dimethylsiloxane) (PDMS), poly(isobutylene) (PIB), poly(ethylene-co-propylene) (E/Pco), poly(styrene-butadiene) (PSB), low density polyethylene (LDPE), polybutadiene cis/trans (PBCT), poly(acrylonitrile-co-butadiene) (PAB), poly(acrylate) (PA), poly (dimethylsiloxane)/poly(divinylbenzene) (PDMS/DVBS), and poly(ethylene glycol)/poly(divinylbenzene) (Carbowax/DVB)), a hydrophilic polymer (e.g., cellulose membranes, polydextranes, and (substituted) poly(ethylene glycol), a molecularly imprinted/templated polymer, and the like.

Figure 2:
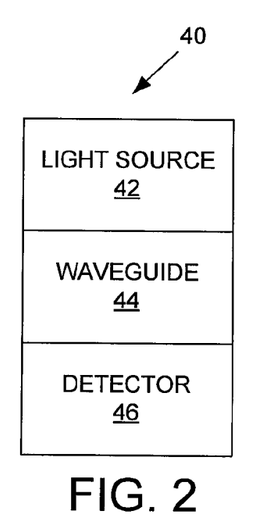
FIG. 2 illustrates a detection system that includes an embodiment of a solid state, thin film waveguide.

FIG. 2 illustrates a detection system that includes, but is not limited to, a light source system 42, a thin film waveguide 44, and a detector system 46. The light source system 42 includes one or more light sources 42. The light source 42 directs light into the thin film waveguide 44. The detector system 46 detects the light emitted at the end of the thin film waveguide 44 (with or without optics). The light source 42 is aligned (e.g., in-line or off-line) with the thin film waveguide 44. The detector system 46 is aligned (e.g., in-line or off-line) with the thin film waveguide 44. The light source system 42, the thin film waveguide 44, and/or the detector system 46 can be all formed on discrete platforms, combinations of two formed on a single platform, or all three formed on a single platform. In an embodiment, the light source system 42, the thin film waveguide 44, and the detector system 46 are formed on a monolithic structure (with or without optics)

The light source 42 can include, but is not limited to, quantum cascade lasers, lead salt laser, $CO_2$ laser, Er:YAG lasers, optical parametric oscillators (OPO), LEDs, and multiwavelength/broadband light sources (e.g., blackbody filaments, SiC filaments, NiCr wires, and the like). The light source 42 can emit light at a single wavelength or at multiple wavelengths. The wavelength can include a single wavelength or multiple wavelengths from about 2 to 1000 μm and any range within this wavelength range, which can include, but is not limited to, about 2 to 5, about 2 to 12, about 5 to 8, about 5 to 12, about 5 to 15, about 5 to 20, about 8 to 12, about 8 to 15, about 8 to 20, about 2 to 15, about 2 to 20, about 10 to 20, about 10 to 50, about 20 to 50, about 20 to 100, about 50 to 100, about 50 to 200, and about 100 to 1000 μm.

In particular, the light source 42 is a quantum cascade laser that can emit at a single wavelength. The wavelength can include, but is not limited to, about 2 to 5, about 2 to 12, about 5 to 8, about 5 to 12, about 5 to 15, about 5 to 20, about 8 to 12, about 8 to 15, about 8 to 20, about 2 to 15, about 2 to 20, and about 10 to 20.

In addition, an optic system (e.g., optics, direct butt-coupling/pig-tailing, integrated optics, grating couplers, prisms, and the like) can be disposed between the light source 42 and the thin film waveguide 44. Optic systems are known in the art.

The thin film waveguide 44 can include a symmetric thin film waveguide (e.g., the symmetric thin film waveguide described in reference to FIG. 1A) and/or an asymmetric thin film thin film waveguide (e.g., the asymmetric thin film waveguides described in reference to FIGS. 1B and 1C). The thin film waveguide 44 can be a single strip thin film waveguide or a planar thin film waveguide, both of which are described in reference to FIGS. 3A and 3B.

The detector 46 can include, but is not limited to cooled or uncooled, thermal detectors (e.g., thermopile, and the like), (photovoltaic or photoconductive) semiconductor detectors (e.g., Hg—Cd—Te detector, InSb detector, Ge detector, and the like), pyroelectric detectors, DTGS detectors, (micro) bolometers, and quantum detectors (e.g., quantum well infrared photoconductive devices (QWIP)). In addition, an optic system (e.g., optics, direct butt-coupling/pig-tailing, integrated optics, grating couplers, prisms, and the like) can be disposed between the thin film waveguide 44 and the detector 46. Optic systems are known in the art.

Figures 3A, 3B:
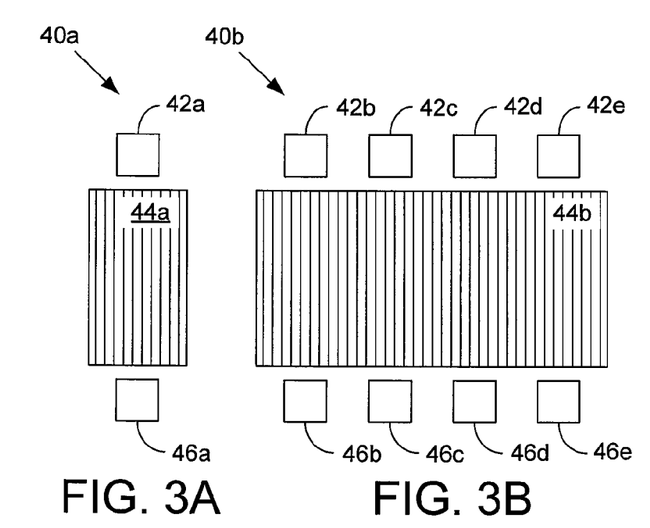
FIG. 3A illustrates a system with a single waveguide.
FIG. 3B illustrates a system with multiple waveguides integrated into one chip, multiple light sources or a linear light source array, and multiple detectors or a line detector array.

FIG. 3A illustrates a top view of a detector system 42a that includes, but is not limited to, a light source 42a, a single strip thin film waveguide 44a, and a detector 46a. The light source 42a directs light into the single strip thin film waveguide 44a. The single strip thin film waveguide 44a has at least a width that contains the light emitted from the light source 42a.

FIG. 3B illustrates a top view of a detector system 42b that includes, but is not limited to, four light sources 42b through 42e, a planar thin film waveguide 44b, and four detectors 46b through 46e. The four light sources 42b through 42e are separated by a distance sufficient to ensure that the light emitted from each of the four light sources 42b through 42e do not overlap or overlaps to an insignificant degree that effects detection of the target compound(s). In other words, each light wave traveling through the planar waveguide 44b does not overlap or overlaps to an insignificant degree. In another embodiment, the number of light sources and detectors can be greater than 2.

While embodiments of the present disclosure are described in connection with Example 1 and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLE

Thin film GaAs waveguides were designed and fabricated by molecular beam epitaxy (MBE) for use in mid-infrared (MIR) evanescent field liquid sensing. Waveguides were designed to facilitate the propagation of a single mode at a wavelength of 10.3 µm emitted from a distributed feedback quantum cascade laser (DFB-QCL), which overlaps with molecular selective absorption features of acetic anhydride. The characterization of the waveguides shows transmission across a broad MIR band. Evanescent field absorption measurements indicate a significant sensitivity enhancement in contrast to multimode planar silver halide waveguides.

The present disclosure demonstrates MIR evanescent field sensors with a new generation of GaAs thin film planar waveguides designed and fabricated to match the emission band of a QCL light source. These single mode IR waveguides are designed to improve the sensitivity of evanescent field absorption measurements, and to provide a platform for the development of highly integrated and miniaturized MIR liquid phase sensing system aiming at incorporating QCL and waveguide on a single chip. The GaAs material has the advantage of exhibiting very low absorption across the whole mid-infrared to a wavelength of about 16 µm where the first multiphonon absorption features are present. The restrahlen band will completely eliminate radiation between about 25-40 µm. Low loss waveguides can be epitaxially grown utilizing the relatively large refractive index step between $Al_xGa_{1-x}As$ and GaAs materials.

Experimental

Chemicals

Acetic anhydride was purchased from Sigma Aldrich (Milwaukee, Wis., USA) at 99.9% purity and acetonitrile was obtained from VWR (West Chester, Pa., USA) at HPLC grade.

Waveguide Fabrication:

The waveguides were fabricated by molecular beam epitaxy on a Si-doped GaAs wafer substrate. The doped substrate was selected to effectively absorb and thereby suppress stray light occurring outside the optical waveguide, as its free carrier absorption is over 300 $cm^{-1}$ at µ=974 $cm^{-1}$. The waveguide included a 6 µm $Al_{0.2}Ga_{0.8}As$ cladding layer, followed by a 6 µm GaAs core layer that completed the epitaxial growth. To passivate the surface against potential etching or corrosion by the sample solution being sensed, a 300 nm $Si_3N_4$ layer was deposited by PECVD at the surface of some waveguide samples.

Figure 4:
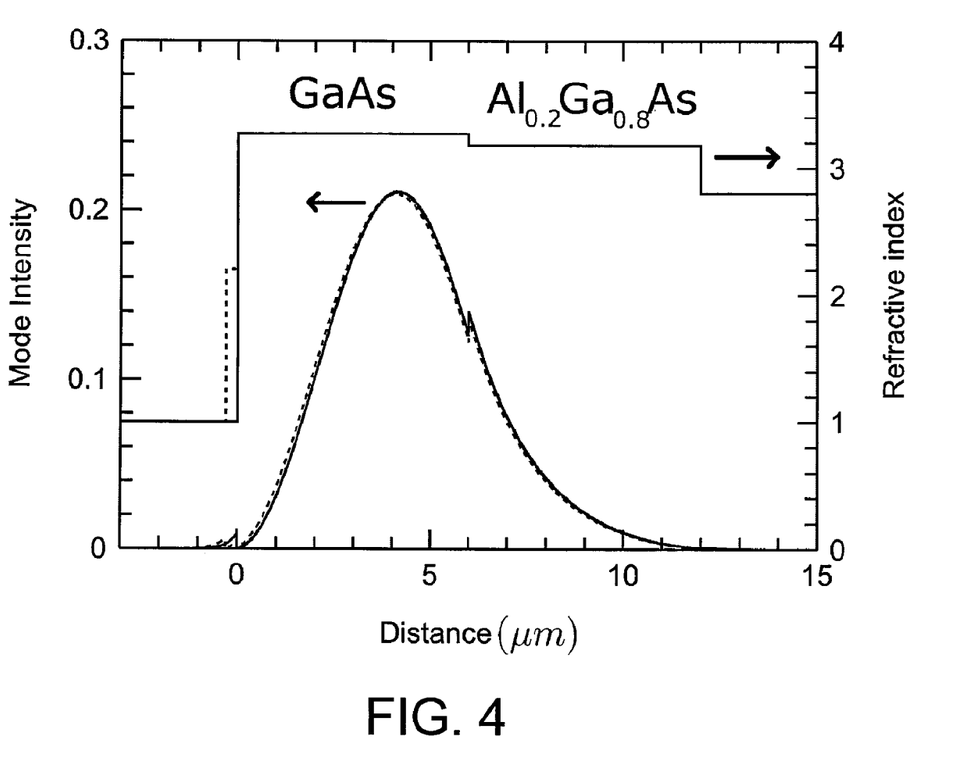
FIG. 4 illustrates the refractive index profile (right axis) and optical mode profile (left axis) for a waveguide without overlayer (e.g., silicone nitride, diamond, diamond-like carbon, and the like).

A schematic of the refractive index distribution of the waveguide structure and a computed optical mode profile for TM polarized light is displayed in FIG. 4. The computed overlap of the evanescent field with a gaseous species (assuming n=1) is 2.3 e-3, decreasing to 1.6 e-3 with the additional $Si_3N_4$ overlayer. In the presence of a liquid with a higher refractive index the overlap value increases accordingly. Larger overlap is achieved for more tightly confined waveguides, however, with the compromise of a large numerical aperture for the mode. The computed waveguide absorption is only 0.27 $cm^{-1}$, which is limited by leakage of the mode inside the n+ doped substrate. This low value of losses enables the application of single-mode planar waveguides with a length of a few centimeters at yet acceptable losses.

Finally, processed wafers were cleaved into strip waveguides by scoring along the crystal axis with a diamond knife and breaking along the score. The waveguides were each 0.5 cm wide and varied in length from 1 to 2.5 cm. The optical quality of the end facets was verified by scanning electron microscopy (SEM). FT-IR spectra were recorded at strip waveguides with a length of 1 cm and a width of 0.5 cm.

FT-IR Measurements

Figure 5:
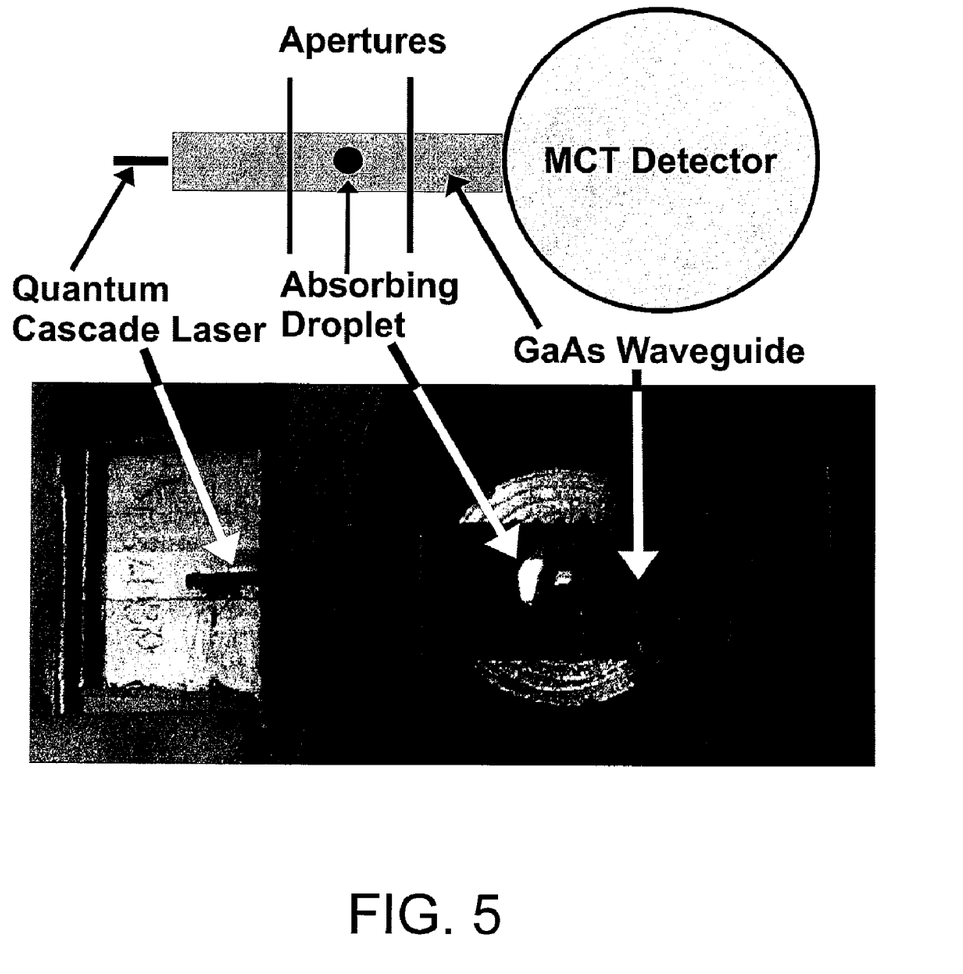
FIG. 5 illustrates the experimental setup for QCL based evanescent field absorption measurements with the QCL pigtail coupled to a GaAs waveguide and a droplet of absorbing analyte at the waveguide surface.

Coupling into waveguide segments was achieved by focusing the collimated unpolarized beam from a FT-IR spectrometer (Bruker IFS 66, Bruker Optics, Billerica, Mass.) onto the waveguide end facet using an off-axis parabolic mirror with a focal length of 3 inches. Light emanating from the distal end of the waveguide was collected by pig-tail coupling of the waveguide to the ZnSe window of a liquid nitrogen cooled MCT detector (Kolmar Technologies, Newburyport, Mass.).
QCL Measurements Evanescent field measurements with GaAs waveguides were demonstrated by coupling with a DFB-QCL (Alpes Lasers, Neuchatel, Switzerland) emitting TM polarized light at 974 $cm^{-1}$ (10.3 μm), which overlaps with the $CH_3$—C bending vibration of acetic anhydride. The laser was operated at a temperature of 10° C., and modulated at a pulse duration of 40 ns with a period of 2.64 μs. During the pulse, the amplitude was controlled by an external power supply set to 22 V. The QCL was pig-tail coupled to the waveguide as shown in FIG. 5. Radiation from the distal end of the waveguide was collected by a MCT detector, similar to the FT-IR experiments.

Acetic anhydride was deposited at the waveguide surface in 0.5 μL droplets, each covering a length of 3 mm at the center of the waveguide surface as shown in FIG. 5. Sequential addition of two more droplets of the same volume and surface area increased the covered waveguide surface area, thereby generating a response curve corresponding to the change in light intensity through the waveguide ($I/I_o$) as a function of the absorbing analyte coverage length along the waveguide surface. For comparison, the evanescent field absorption measurements were repeated at the surface of a multimode silver halide planar waveguide with a thickness of 300 μm (width: 3 mm; length: 35 mm). Light was coupled into the silver halide waveguide at or near the critical angle resulting in the most sensitive evanescent field measurements achievable with this waveguide.

Acetonitrile, which does not absorb at the 10.3 μm emission wavelength of the QCL was also deposited at the surface of both waveguides verifying no damping of the laser radiation due to the solvent. Hence, it was confirmed that the signal change in the case of acetic anhydride deposition exclusively results from molecule specific absorption rather than the refractive index modulation effects.

Results and Discussion

Figure 6:
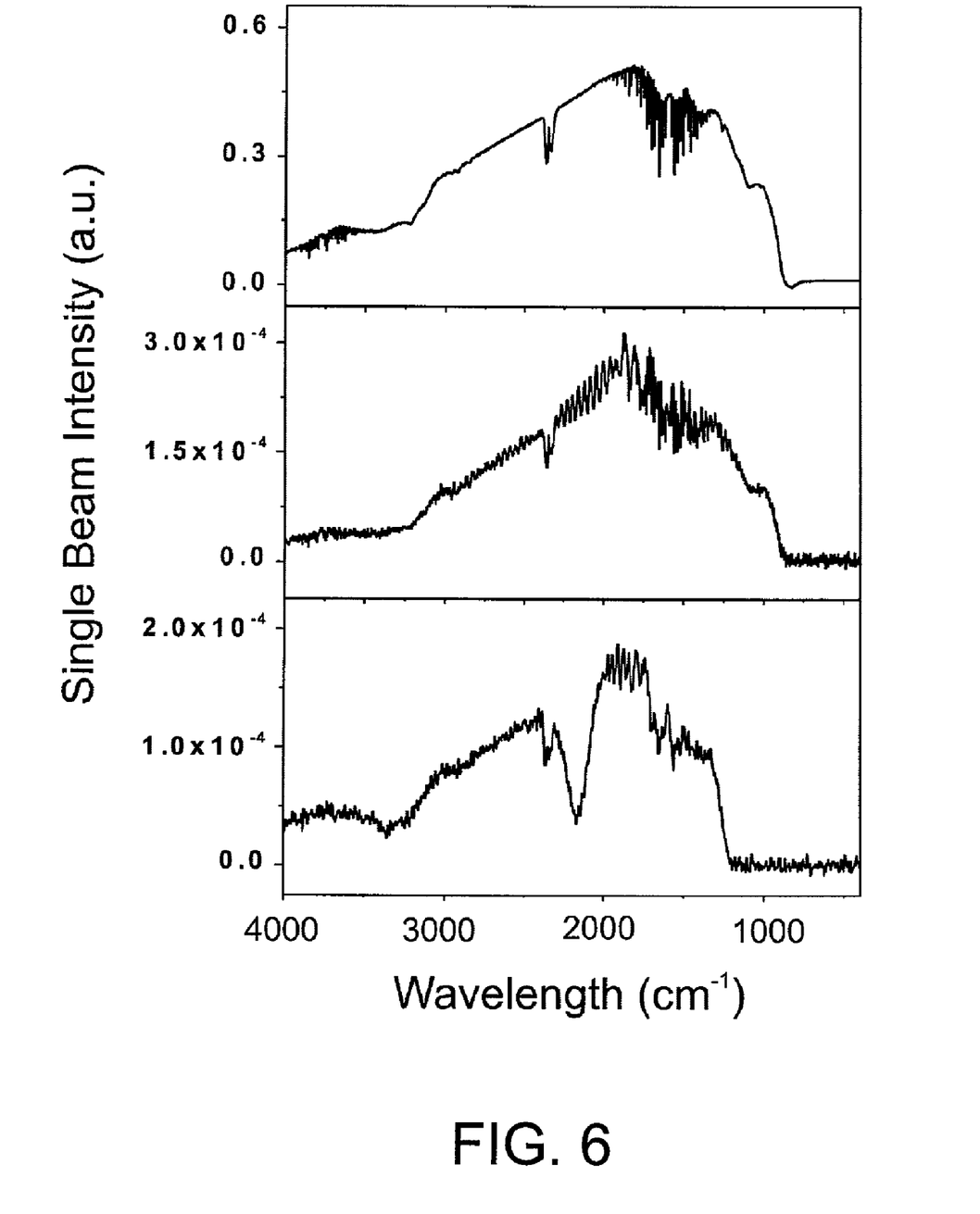
FIG. 6 illustrates FT-IR spectra recorded with (top) no waveguide, (middle) a GaAs waveguide, and (bottom) a GaAs waveguide with silicone nitride overlayer.

FIG. 6 shows single beam FT-IR transmission spectra recorded by coupling radiation through the long axis of different waveguides with and without silicon nitride overlayer, respectively. For reference, a detector response curve without waveguide is provided. All spectra show characteristic gaseous $CO_2$ features at about 2300 $cm^{-1}$, and water vapor bands at approximately 1600 $cm^{-1}$ and 3700 $cm^{-1}$ resulting from the ambient environment. The spectra recorded through the waveguides are characterized by much lower signal-to-noise ratios, due to the comparatively small amount of radiation coupled into these thin film planar waveguide structures. It is evident, that besides the decrease in transmitted light energy, no change of the spectral transmission window is occurring in comparison between the GaAs waveguide and the detector response curve. These spectra reveal that despite being optimized to transmit light at 10.3 μm, broadband IR light is still propagated by the waveguide. However, the spectra for the waveguide overcoated with silicon nitride clearly reveal solid state absorption features centered at 2150 $cm^{-1}$, and a shifted transmission cut-off wavelength at 1250 $cm^{-1}$ resulting from the additional $Si_3N_4$ layer.

Figure 7:
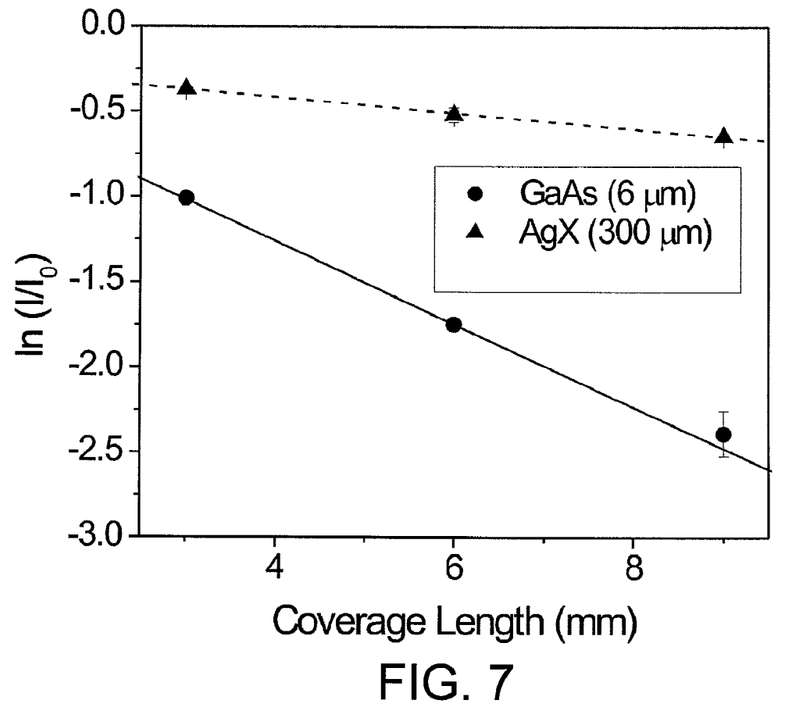
FIG. 7 illustrates a system response for a GaAs waveguide (●) and a silver halide (AgX) waveguide (♦) as a function of the waveguide surface coverage area along with linear regression fits.

Response curves for both waveguides are shown in FIG. 7; the circular symbols represent the response obtained with the GaAs waveguide fitted with a linear regression function (solid line). The response for the silver halide waveguide is indicated with triangular symbols and a dashed linear regression fit. In comparing the slopes of the two linear fits, it is shown that the GaAs response function has a slope of 0.24, while the slope of the response function for the silver halide waveguide is 0.05. Hence, an improvement in evanescent field sensitivity by a factor of 5 is clearly evident for the single mode GaAs waveguide. This increase in sensitivity obtained from the thin film GaAs waveguide is attributed to an increase in r, which is the fractional radiation power guided outside the core of the single mode waveguide. In this context, it should be considered that the current waveguide structure is optimized for low loss rather than maximum overlap. Hence, it is expected that by increasing r an improved sensitivity by one order of magnitude or more can be achieved.

The theoretical change in transmission achievable with the GaAs waveguide was calculated at 0.803 using the Lambert-Beer law based on an extinction coefficient for acetic anhydride of 2.69 L/mol*mm. This value was obtained from IR transmission spectroscopy of the pure analyte recorded at an optical path length of 3 mm, which corresponds to the diameter of a single droplet deposited at the waveguide surface, and a fractional evanescent field power of 2.3 e-3. The experimentally obtained value for a single droplet at the GaAs waveguide surface is 0.638. The difference between the calculated and the experimentally obtained value is attributed to edge effects such as scattering resulting from the confined droplet at the waveguide surface.

Figure 8:
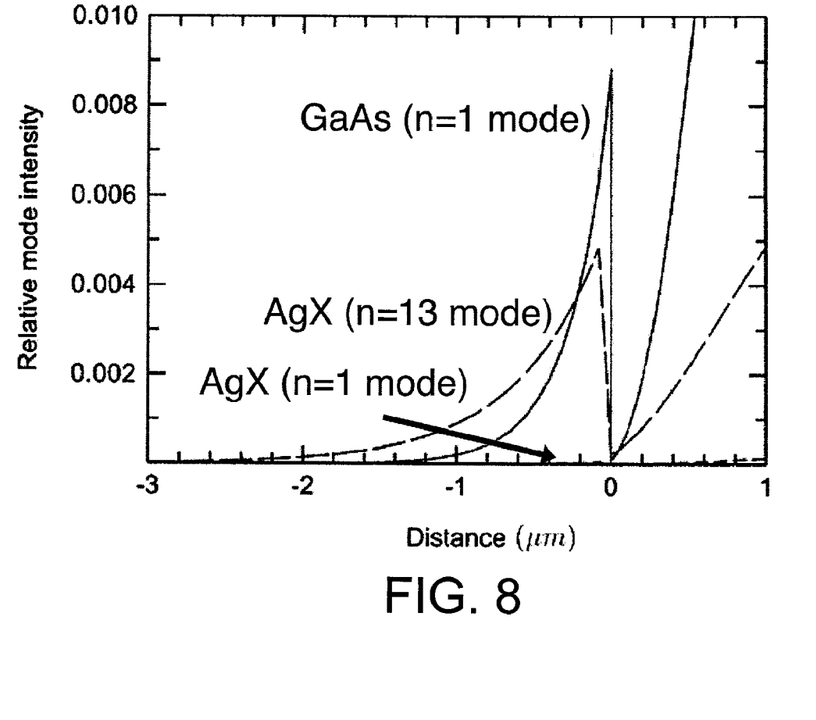
FIG. 8 illustrates the relative mode intensity for TM polarized light as a function of distance perpendicular to the direction of propagation for GaAs fundamental mode (solid), AgX high order mode (long dash), and AgX fundamental mode (short dash) with the region <0 located outside the waveguide (evanescent field).

In addition to the sensitivity improvement achieved with the single mode GaAs waveguides, improved control on the evanescent field is prevalent for this novel waveguide structure facilitating quantitative measurements at the waveguide surface. As each individual mode propagating through a waveguide has a distinct evanescent field profile, multimode waveguides are characterized by a distribution of evanescent field intensities and profiles, which strongly depend on the coupling conditions, among other factors. A waveguide supporting only a single mode as fabricated in this study provides a well-defined evanescent field independent of the coupling conditions. FIG. 8 shows a plot of the calculated relative mode intensity as a function of distance perpendicular to the direction of propagation for TM polarized light. The distance from zero in the negative direction corresponds to the radiation guided in the evanescent field. Mode profiles are shown for the single mode supported by the GaAs waveguide developed in this study, along with a high order mode (n=13) and a low order mode (n=1) for a multimode silver halide waveguide. The low order mode profile for silver halide is very near the axis due to its low intensity relative to the high order mode revealing the substantial difference in evanescent field intensities of multimode waveguides. The GaAs waveguide supports only the mode indicated by the solid line, which facilitates quantitative measurements in contrast to multimode silver halide waveguides due to a precisely defined and tunable mode structure. Furthermore, the high intensity of the evanescent mode component characteristic for the GaAs waveguide near the surface (distance=0) compared to any mode of the silver halide waveguide is noteworthy. This allows for particularly sensitive measurements at the waveguide surface such as for monolayers of molecules. The high intensity at the waveguide surface and the sharp decay are due to the large refractive index contrast between the waveguide and the probed surface layer, as predicted by theory.

CONCLUSION

In conclusion, the first thin film GaAs single mode IR waveguides are designed and fabricated matching the emission frequency of a DFB-QCL at 10.3 μm, demonstrating MIR evanescent field liquid phase sensing. Evanescent field absorption measurements reveal a marked increase in sensitivity in contrast to multimode silver halide waveguides, and the ability to detect acetic anhydride serving as exemplary analyte at the waveguide surface. Furthermore, these waveguides provide a well-defined evanescent field at the waveguide surface with a sharp decrease into the surrounding material rendering them ideal for sensitive and quantitative measurements of molecular monolayers deposited at the waveguide surface. These next-generation planar IR waveguides show substantial promise toward entirely integrated on-chip infrared chemical sensing platforms combining a single mode-matched thin film waveguide ideally grown on the same substrate as the QCL for highly integrated MIR liquid phase sensing platforms.

Although the methodologies of this disclosure have been particularly described in the foregoing disclosure, it is to be understood that such descriptions have been provided for purposes of illustration only, and that other variations both in form and in detail can be made thereupon by those skilled in the art without departing from the spirit and scope of the present invention, which is defined solely by the appended claims.

What is claimed is:

1. An evanescent field absorption, symmetrical solid state, thin film waveguide comprising:
a substrate having a core layer disposed thereon, the core layer has a thickness of about 2 to 1000 μm, wherein the core layer is made of a material selected from: group III-V materials, composites thereof, and combinations thereof, wherein the waveguide is configured so that an evanescent field of light protrudes from the core layer on the side opposite the substrate, wherein the evanescent field of light interacts with a sample disposed adjacent the core.

2. The symmetrical solid state, thin film waveguide of claim 1, wherein the core layer has a thickness selected from: about 2 to 5, about 2 to 12, about 5 to 8, about 5 to 12, about 5 to 15, about 5 to 20, about 8 to 12, about 8 to 15, about 8 to 20, about 2 to 15, about 2 to 20, and about 10 to 20 μm.

3. The symmetrical solid state, thin film waveguide of claim 1, wherein the core layer has a thickness selected from: about 10 to 50, about 20 to 50, about 20 to 100, about 50 to 100, and about 50 to 200 μm.

4. The symmetrical solid state, thin film waveguide of claim 1, wherein the core layer has a thickness of about 100 to 1000 μm.

5. The symmetrical solid state, thin film waveguide of claim 1, wherein the material is selected from: GaAs, AlGaAs, AlAsSb, InAs, InP, InSb, Sb, InSb, AlAs, AlInAs, GaInAs, AlSb, GaSb, InAs, SiGe, GaN, AlN, AlGaN, InGaN, and GaP.

6. The symmetrical solid state, thin film waveguide of claim 1, further comprising a protective layer disposed on the core layer, wherein the evanescent field of light protrudes from the core layer and the protective layer.

7. An evanescent field absorption, asymmetrical solid state, thin film waveguide comprising:
a substrate, a cladding layer, and a core layer, wherein the cladding layer is disposed on the substrate, wherein the core layer is disposed on the cladding layer, wherein the combination of the thickness of the core layer and the cladding layer is about 2 to 1000 μm, wherein the core layer is made of a first material selected from: group III-V materials, composites thereof, and combinations thereof, wherein the cladding layer is made of a second material selected from: group III-V materials, composites thereof, and combinations thereof, wherein the core layer and the cladding layer have different refractive indices, wherein the waveguide is configured so that an evanescent field of light protrudes from the core layer, wherein the evanescent field of light is asymmetrically positioned within the core layer and the cladding layer so that unequal portions of an evanescent tail of the evanescent field of light extends out of the top and bottom of the core layer, wherein the evanescent field of light interacts with a sample disposed adjacent the core.

8. The asymmetrical solid state, thin film waveguide of claim 7, wherein each of the cladding layer and the core layer have a thickness selected from: about 2 to 5, about 2 to 12, about 5 to 8, about 5 to 12, about 5 to 15, about 5 to 20, about 8 to 12, about 8 to 15, about 8 to 20, about 2 to 15, about 2 to 20, and about 10 to 20 μm.

9. The asymmetrical solid state, thin film waveguide of claim 7, wherein each of the cladding layer and the core layer have a thickness selected from: about 10 to 50, about 20 to 50, about 20 to 100, about 50 to 100, and about 50 to 200 μm.

10. The asymmetrical solid state, thin film waveguide of claim 7, wherein each of the cladding layer and the core layer have a thickness of about 100 to 1000 μm.

11. The asymmetrical solid state, thin film waveguide of claim 7, wherein each of the first material and the second material are independently selected from: GaAs, AlGaAs, AlAsSb, InAs, InP, InSb, Sb, InSb, AlAs, AlInAs, GaInAs, AlSb, GaSb, InAs, SiGe, GaN, AlN, AlGaN, InGaN, and GaP, wherein the first material and the second material are different materials and have different refractive indices.

12. The asymmetrical solid state, thin film waveguide of claim 7, further comprising a protective layer disposed on the core layer, wherein the protective layer is selected from: $Si_3N_4$, $SiO_2$, diamond, carbon-like diamond, polymers, and combinations thereof, wherein the evanescent field of light protrudes from the core layer and the protective layer.

* * * * *